(12) United States Patent
Luu et al.

(10) Patent No.: US 7,803,746 B2
(45) Date of Patent: Sep. 28, 2010

(54) ANTIMICROBIAL FOAM HAND SOAP COMPRISING INULIN OR AN INULIN SURFACTANT

(75) Inventors: Phuong V. Luu, Appleton, WI (US); David W. White, Clintonville, WI (US); Michael A. Sturm, Menasha, WI (US)

(73) Assignee: Georgia-Pacific Consumer Products LP, Atlanta, GA (US)

( * ) Notice: Subject to any disclaimer, the term of this patent is extended or adjusted under 35 U.S.C. 154(b) by 0 days.

(21) Appl. No.: 12/214,013

(22) Filed: Jun. 16, 2008

(65) Prior Publication Data

US 2008/0255014 A1 Oct. 16, 2008

Related U.S. Application Data

(63) Continuation-in-part of application No. 11/304,353, filed on Dec. 15, 2005, now Pat. No. 7,521,404.

(60) Provisional application No. 60/637,101, filed on Dec. 16, 2004, provisional application No. 60/936,621, filed on Jun. 21, 2007.

(51) Int. Cl.
C11D 1/90 (2006.01)
C11D 3/22 (2006.01)

(52) U.S. Cl. .................. 510/138; 510/130; 510/131; 510/155; 510/156; 510/370; 510/382; 510/426; 510/427; 510/470; 510/490

(58) Field of Classification Search ............... 510/130, 510/131, 138, 155, 156, 370, 382, 426, 427, 510/470, 490
See application file for complete search history.

(56) References Cited

U.S. PATENT DOCUMENTS

| | | | | |
|---|---|---|---|---|
| 4,753,749 A | | 6/1988 | McIntosh .................... 510/382 |
| 5,503,779 A | * | 4/1996 | Adamy et al. ............... 510/427 |
| 5,514,369 A | * | 5/1996 | Salka et al. ................. 424/70.1 |
| 5,580,850 A | * | 12/1996 | Bigorra Llosas et al. .... 510/504 |
| 5,614,180 A | * | 3/1997 | Chung ..................... 424/70.19 |
| 5,635,462 A | | 6/1997 | Fendler et al. .............. 510/131 |
| 5,635,469 A | | 6/1997 | Fowler et al. ............... 510/406 |
| 5,646,100 A | * | 7/1997 | Haugk et al. ................ 510/131 |
| 5,683,683 A | | 11/1997 | Scafidi ..................... 424/70.19 |
| 5,686,400 A | * | 11/1997 | Urfer et al. ................. 510/237 |
| 5,688,752 A | | 11/1997 | Turner ........................ 510/159 |
| 5,709,872 A | | 1/1998 | Van Rees |
| 5,719,113 A | * | 2/1998 | Fendler et al. .............. 510/382 |
| 5,741,769 A | * | 4/1998 | Erilli .......................... 510/417 |
| 5,767,051 A | * | 6/1998 | Drapier et al. .............. 510/235 |
| 5,781,942 A | | 7/1998 | Allen et al. ..................... 4/623 |
| 5,792,737 A | * | 8/1998 | Gruning et al. ............. 510/126 |
| 5,804,203 A | | 9/1998 | Hahn et al. |
| 5,945,910 A | | 8/1999 | Gorra ....................... 340/573.1 |
| 6,022,551 A | | 2/2000 | Jampani et al. |
| 6,046,145 A | * | 4/2000 | Santora et al. .............. 510/121 |
| 6,051,542 A | * | 4/2000 | Pollack et al. .............. 510/426 |
| 6,162,423 A | * | 12/2000 | Sebag et al. .............. 424/70.12 |
| 6,224,886 B1 | * | 5/2001 | Charlton et al. ............. 424/401 |
| 6,296,880 B1 | | 10/2001 | Murad |
| 6,331,293 B1 | | 12/2001 | Smith et al. ................... 424/59 |
| 6,346,252 B1 | * | 2/2002 | Moigne ................. 424/195.17 |
| 6,383,523 B1 | | 5/2002 | Murad |
| 6,451,775 B1 | | 9/2002 | Sith et al. ...................... 514/77 |
| 6,565,615 B1 | * | 5/2003 | Wong et al. .................... 8/408 |
| 6,613,755 B2 | | 9/2003 | Peterson et al. ............... 514/63 |
| 6,627,612 B1 | | 9/2003 | O'Lenick, Jr. et al. ........ 514/25 |
| 6,881,710 B1 | | 4/2005 | O'Lenick, Jr. et al. ...... 510/123 |
| 7,256,165 B2 | * | 8/2007 | Bertrem et al. ............. 510/189 |
| 7,417,020 B2 | * | 8/2008 | Fevola et al. ............... 510/475 |
| 2001/0042761 A1 | | 11/2001 | Ophardt et al. ............. 222/190 |
| 2002/0002124 A1 | | 1/2002 | Biedermann et al. ........ 510/218 |
| 2002/0012648 A1 | | 1/2002 | Orthoefer ................ 424/70.27 |
| 2002/0022660 A1 | | 2/2002 | Jampani et al. |
| 2002/0061500 A1 | | 5/2002 | Collopy ...................... 434/238 |
| 2002/0071818 A1 | * | 6/2002 | Cole et al. ................. 424/70.1 |
| 2002/0103092 A1 | | 8/2002 | Tashjian et al. ............. 510/130 |
| 2002/0141959 A1 | | 10/2002 | Peterson et al. .......... 424/70.12 |
| 2002/0165104 A1 | * | 11/2002 | Santora et al. .............. 510/130 |
| 2002/0169099 A1 | * | 11/2002 | Knox et al. ................. 510/421 |
| 2003/0031727 A1 | | 2/2003 | Hahn et al. |
| 2003/0069148 A1 | * | 4/2003 | Booker et al. .............. 510/130 |
| 2003/0114323 A1 | * | 6/2003 | Booker et al. .............. 510/130 |
| 2004/0009885 A1 | * | 1/2004 | Davies et al. ............... 510/279 |
| 2004/0146481 A1 | * | 7/2004 | Busch et al. .................. 424/74 |

(Continued)

OTHER PUBLICATIONS

Colonial Chemical, Inc. product bulletin entitled "Colalipid Products", pp. 1-5, revised Feb. 13, 2003.

(Continued)

*Primary Examiner*—Charles I Boyer
(74) *Attorney, Agent, or Firm*—Joel T. Charlton

(57) ABSTRACT

An antimicrobial foam hand soap composition includes a glutinous component to promote more thorough hand washing. The glutinous component may be selected from the group consisting of: cocamidopropyl PG-dimonium chloride phosphate; dimer dilinoleamido-propyl PG-dimonium chloride phosphate; sodiumgrapeseedamidopropyl PG-dimonium chloride phosphate; sodium olivamidopropyl PG-dimonium chloride phosphate; linoleamidopropyl PG-dimonium chloride phosphate; PEG-8 dimethicone sunfloweramidopropyl PG-dimonium complex; sunfloweramidopropyl phosphate PG-dimonium chloride, inulin, inulin-based surfactants and mixtures thereof. Polysaccharide-based or natural oil-based foaming agents and surfactants are suitably included in the compositions.

1 Claim, 3 Drawing Sheets

U.S. PATENT DOCUMENTS

| | | | |
|---|---|---|---|
| 2005/0101515 A1 | 5/2005 | Pawson et al. | |
| 2005/0180939 A1* | 8/2005 | Fonolla Moreno | 424/70.13 |
| 2006/0011655 A1 | 1/2006 | Ophardt | 222/190 |
| 2006/0135384 A1 | 6/2006 | Luu et al. | 510/130 |
| 2006/0135393 A1* | 6/2006 | Molenda | 510/421 |
| 2006/0147406 A1* | 7/2006 | Yerby et al. | 424/70.24 |
| 2006/0228317 A1* | 10/2006 | Chrisstoffels et al. | 424/70.7 |
| 2006/0233737 A1* | 10/2006 | Janailhac et al. | 424/74 |
| 2007/0160652 A1* | 7/2007 | Mueller et al. | 424/443 |
| 2007/0292383 A1* | 12/2007 | Schepky et al. | 424/78.03 |
| 2008/0014154 A1* | 1/2008 | Mougin et al. | 424/59 |
| 2008/0167494 A1* | 7/2008 | Teixeira Tage Biaggio et al. | 562/512 |
| 2008/0242739 A1* | 10/2008 | Kroon et al. | 514/781 |
| 2008/0260674 A1* | 10/2008 | Philippe | 424/70.13 |
| 2008/0261844 A1* | 10/2008 | Ruppert et al. | 510/158 |
| 2008/0305192 A1* | 12/2008 | Brand et al. | 424/756 |
| 2009/0175761 A1 | 7/2009 | Luu et al. | |

OTHER PUBLICATIONS

PCT International Search Report and Written Opinion of the International Search Authority for PCT/US2009/047354 mailed Jan. 25, 2010.

* cited by examiner

0 SECOND

30 SECOND

60 SECOND

0 SECOND

30 SECOND

60 SECOND

ANTIMICROBIAL FOAM HAND SOAP COMPRISING INULIN OR AN INULIN SURFACTANT

CROSS-REFERENCE TO RELATED CASES

This application is based upon U.S. Provisional Application Ser. No. 60/936,621, filed Jun. 21, 2007, of the same title. This application is also a continuation-in-part application of U.S. patent application Ser. No. 11/304,353, filed Dec. 15, 2005, entitled "Antimicrobial Liquid Hand Soap Compositions With Tactile Signal", now U.S. Pat. No. 7,521,404. U.S. patent application Ser. No. 11/304,353, now U.S. Pat. No. 7,521,404, was based upon U.S. Provisional Application Ser. No. 60/637,101, filed Dec. 16, 2004. The priorities of the foregoing applications are hereby claimed and their disclosures incorporated herein by reference.

TECHNICAL FIELD

The present invention relates generally to foam hand soap and more particularly to antimicrobial foam hand soap with glutinous components which provide a tactile signal to promote more thorough contact with the skin so as to enhance antimicrobial activity.

BACKGROUND OF THE INVENTION

Media attention to cases of food poisoning, strep infections, and the like due to microbial contamination has increased public awareness of the dangers posed by inadequate hygiene, particularly in the food service and health industries. Bacteria found on the skin can be divided into two groups: resident and transient bacteria. Resident bacteria are Gram positive bacteria which are established as permanent microcolonies on the surface and outermost layers of the skin and play an important, helpful role in preventing the colonization of other, more harmful bacteria and fungi. Transient bacteria are bacteria which are not part of the normal resident flora of the skin, but can be deposited when airborne contaminated material lands on the skin or when contaminated material is brought into physical contact with it. Transient bacteria are also typically divided into Gram positive and Gram negative subclasses. Gram positive bacteria include pathogens such as *Staphylococcus aureus, Streptococcus pyogenes* and *Clostridium botulinum*. Gram negative bacteria include pathogens such as *Salmonella, Escherichia coli, Klebsiella, Haemophilus, Pseudomonas aeruginosa, Proteus* and *Shigella dysenteriae*. Gram negative bacteria are generally distinguished from Gram positive by an additional protective cell membrane which generally results in the Gram negative bacteria being less susceptible to topical antibacterial actives. The American Society of Microbiologists has indicated that adequate hand washing will greatly reduce the incidence of communicable diseases.

Washing of the skin, especially the hands, with antimicrobial soap formulations can remove many viruses and bacteria from the washed surfaces. Removal of the viruses and bacteria is due to the surfactancy of the soap and the mechanical action of the wash procedure. Therefore, it is known and recommended that the people wash frequently to reduce the spread of viruses and bacteria. Recent surveys, however, have revealed that while nearly 95% of people claim to have washed their hands after use of public restrooms, actual observations reveal that this figure does not exceed about 66%. Notwithstanding increased awareness, there is a tendency to rush the hand washing process which leads to inadequate hygiene. A number of systems and devices to encourage longer and more thorough handwashing have accordingly been developed.

Collopy in United States Patent Application 2002/0061500 discloses a hand-washing device containing a display panel that encourages the user to wash their hands for about 15 seconds to remove germs. Gorra, U.S. Pat. No. 5,945,910 discloses method and apparatus for monitoring and reporting hand washing, which includes a sensor for signaling the dispensation of a cleaning agent from a dispenser, and a reporting and monitoring module. Allen et al. U.S. Pat. No. 5,781,942 discloses wash stations and method of operation, which monitors hand washing and assists in hand washing. These systems are relatively expensive and difficult to implement; oftentimes involving training and monitoring personnel. Even when such steps have been taken, there is little certainty that all personnel have followed proper washing procedures.

So also, while many antimicrobial liquid hand soap compositions have been proposed, effectiveness of antimicrobial agents in the soap may be limited by the thoroughness of the washing procedure as is appreciated by reference to the patents and publications of the preceding paragraph. Another drawback of liquid compositions is that liquid soap tends to be difficult to apply to a targeted area such that it is retained on the desired surface. That is to say, liquid soap tends to drip off the hands before lathering and thus much of the antimicrobial activity of the composition is lost even before the hand washing process has been effectively started.

SUMMARY OF THE INVENTION

The present invention is directed generally to an antimicrobial foam hand soap composition including a glutinous component to promote more thorough hand washing. The glutinous component may be selected from the group consisting of: cocamidopropyl PG-dimonium chloride phosphate; dimer dilinoleamido-propyl PG-dimonium chloride phosphate; sodiumgrapeseedamidopropyl PG-dimonium chloride phosphate; sodium olivamidopropyl PG-dimonium chloride phosphate; linoleamidopropyl PG-dimonium chloride phosphate; PEG-8 dimethicone sunfloweramidopropyl PG-dimonium complex; sunfloweramidopropyl phosphate PG-dimonium chloride, inulin, inulin-based surfactants and mixtures thereof.

While any suitable biocide may be used in the compositions, preferred are those which include halogenated aromatic compounds. One preferred ingredient, for example, is:

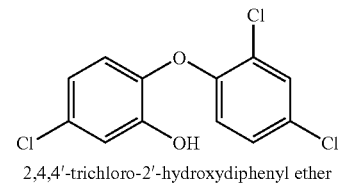

2,4,4'-trichloro-2'-hydroxydiphenyl ether

In another aspect of the invention, there is provided an aqueous foam hand soap composition suitable for air-foaming including: (a) more than 75% water; (b) a polysaccharide or polysaccharide surfactant selected from inulin, inulin surfactants, polyglucoside surfactants and mixtures thereof; and (c) at least one additional foaming surfactant selected from betaine surfactants, wherein the composition includes at least 5% of inulin, inulin surfactants, polyglucoside surfactants or mixtures thereof and the components are selected and present in amounts such that the composition exhibits a liquid viscosity at room temperature of from about 2.5 cps to about 35 cps as well as a 60-second foam stability of at least 0.5.

BRIEF DESCRIPTION OF DRAWINGS

The invention is described in detail below in connection with the various Figures, wherein.

DETAILED DESCRIPTION OF THE INVENTION

Figure 1A:
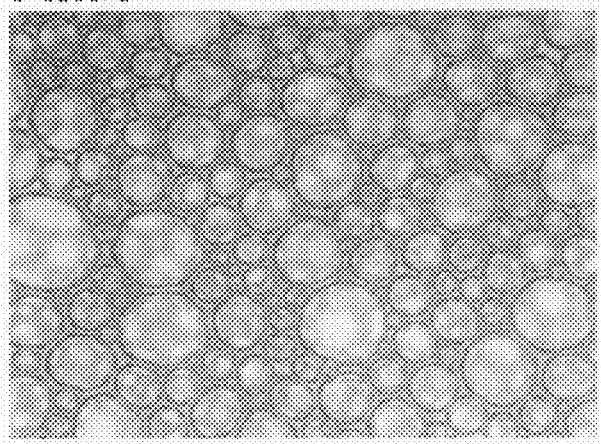
FIGS. 1A, 1B and 1C are photomicrographs of Foamed Composition No. 1 at 0, 30 and 60 seconds, respectively.

The invention is described in detail below for purposes of illustration only. Modifications within the spirit and scope of the invention, set forth in the appended claims, will be readily apparent to one of skill in the art.

As used herein, terminology is given its ordinary meaning as supplemented below. "Room temperature", for example, means 70° F. (about 21° C.).

"Antimicrobial agent", "biocide" and the like terminology means and includes any substance that kills or inhibits the growth of microorganisms such as bacteria, viruses, molds, slimes, fungi, etc. Biocidal chemicals include halogenated aromatics, chlorinated hydrocarbons, organometallics, metallic salts, organic sulfur compounds, quaternary ammonium compounds, phenolics and the like. Suitable biocides include triclosan, the structure of which appears above. Other suitable biocides include: 3,4,4'-trichlorocarbanilide (triclocarban); 3,4,4'-trifluoromethyl-4,4'-dichlorocarbanilide (cloflucarban); 5-chloro-2-methyl-4-isothiazolin-3-one; iodopropynlbutylcarbamate; 8-hydroxyquinoline; 8-hydroxyquinoline citrate; 8-hydroxyquinoline sulfate; 4-chloro-3,5-xylenol(chloroxylenol); 2-bromo-2-nitropropane-1,3-diol; diazolidinyl urea; butoconazole; nystatin; terconazole; nitrofurantoin; phenazopyridine; acyclovir; clortrimazole; chloroxylenol; chlorhexidine; miconazole; terconazole; butylparaben; ethylparaben; methylparaben; methylchloroisothiazoline; methylisothiazoline; a mixture of 1,3-bis(hydroxymethyl)-5,5-dimethylhydantoin and 3-iodo-2-propynyl butyl carbamate; oxyquinoline; EDTA; tetrasodium EDTA; p-hydroxyl benzoic acid ester; alkyl pyridinum compounds; coco phosphatidyl PG-dimonium chloride; chlorhexidine gluconate; chlorhexidine digluconate; chlorhexidine acetate; chlorhexidine isethionate; chlorhexidine hydrochloride; benzalkonium chloride; benzethonium chloride; polyhexamethylene biguanide; and mixtures thereof. So also, the anti-microbial agent may include a zinc salt.

"Glutinous component" means one or more components added to the hand soap composition in order to alter its tactile properties. Some preferred glutinous components are available from Colonial Chemical Inc. and are listed below in Table 1.

TABLE 1

| COLA-LIPID ™ | Chemical Description | Oil Source | Primary R-Group |
|---|---|---|---|
| C | Cocamidopropyl PG-Dimonium Chloride Phosphate | Coconut | Cocamidopropyl |

TABLE 1-continued

Glutinous Phospholipids

| COLA-LIPID ™ | Chemical Description | Oil Source | Primary R-Group |
|---|---|---|---|
| SAFL | Linoleamidopropyl PG-Dimonium Chloride Phosphate | Safflower | Linoleamidopropyl |
| SUN | Sunfloweramidopropyl Phosphate PG-Dimonium Chloride | Sunflower | Linoleamidopropyl |
| OL | Sodium Olivamidopropyl PG-Dimonium Chloride Phosphate | Olive | Oleamidopropyl |
| DLO | Dimer Dilinoleamidopropyl PG-Dimonium Chloride Phosphate | Dimer Acid | Di-Linoleamidopropyl |
| SIL | PEG-8 Dimethicone Sunfloweramidopropyl PG-Dimonium Complex | Sunflower | Silicone and Linoleamidopropyl |
| GS | Sodiumgrapeseedamidopropyl PG-Dimonium Chloride Phosphate | Grapeseed | Linoleamidopropyl |

Further details may be seen in U.S. Pat. No. 6,331,293 to Smith et al., as well as U.S. Pat. No. 6,451,775, also to Smith et al., the disclosures of which are incorporated herein by reference.

Other classes of preferred glutinous components for the inventive foams are inulins and inulin-based surfactants available from ORAFTI (Tienen, Belgium) such as INUTEC H25 and INUTEC SP1.

Among foaming agents suitable for use in the compositions of the present invention, betaines are particularly useful. Suitable betaines may include: the higher alkyl betaines, such as coco dimethyl carboxymethyl betaine, lauryl dimethyl carboxymethyl betaine, lauryl dimethyl alphacarboxyethyl betaine, cetyl dimethyl carboxymethyl betaine, lauryl bis-(2-hydroxyethyl) carboxymethyl betaine, stearyl bis-(2-hydroxypropyl) carboxymethyl betaine, oleyl dimethyl gamma-carboxypropyl betaine, lauryl bis-(2-hydroxypropyl)alpha-carboxyethyl betaine, coco dimethyl sulfopropyl betaine, stearyl dimethyl sulfopropyl betaine, lauryl dimethyl sulfoethyl betaine, lauryl bis-(2-hydroxyethyl) sulfopropyl betaine, and amidobetaines and amidosulfobetaines (wherein the $RCONH(CH_2)_3$ radical is attached to the nitrogen atom of the betaine), oleyl betaine and cocamidopropyl betaine.

Particularly suitable surfactants for use in the composition with a betaine foaming agent include polysaccharide surfactants such as alkyl glucosides seen in U.S. Pat. No. 6,881,710 to O'Lenick, Jr. et al. and U.S. Pat. No. 6,627,612, also to O'Lenick, Jr. et al., the disclosures of which are incorporated herein by reference. The '710 patent relates to polyglucoside quaternary surfactants sold under the Suga®Quat name by Colonial Chemicals, while the '612 patent relates to polyglucoside sulfonate surfactants sold by Colonial Chemicals under the Suga®Nate name. Other suitable surfactants are natural oil isethionates such as cocoyl methyl isothionate available from Innospec (Edison, N.J.). Chelating agents are also used in many compositions, a suitable chelating agent is trisodium ethylene diamine disuccinate, for example.

Further components include the optional components listed in the Examples as well as humectants, emollients and the like which are described in U.S. Pat. No. 5,635,469 to Fowler et al., the disclosure of which is incorporated herein by reference.

EXAMPLES

The following compositions were prepared by mixing the components to a well-mixed aqueous dispersion. Optional components are typically provided in amounts of less than or equal to 0.02% by weight.

TABLE 2

Antimicrobial Foam Soap Composition 1

| Component | Ingredient | Wt. % |
|---|---|---|
| Foamer | Cocamidopropyl Betaine | 1.50 |
| Foam booster, foam stabilizer | Tauranol ®SCMI-85 (Sodium Methyl Isethionate) | 4.00 |
| Foam stabilizer, cleanser, sticky agent | Inutec ® SP1 (Inulin Lauryl Carbamate) | 0.50 |
| Nonionic Skin Conditioner, sticky agent | Inutec ® H25 (Inulin) | 0.50 |
| Chelating Agent | Octaquest ® E30 (Trisodium Ethylenediamine Disuccinate) | 0.20 |
| Antibacterial Agent | Triclosan | 0.50 |
| Humectant | Propylene glycol; | 1.00 |
| Botanical Extracts - Moisturing and Wound Healing | Allantoin ((2,5-Dioxo-4-Imidazolidinyl) urea) | 0.02 |
| Botanical Extracts - Moisturing and Wound Healing | *Aloe Vera* | 0.02 |
| | Vitamin E | Optional |
| Freshness Handfeel | Frescolat ® MGA (Menthone Glycerin Acetal) | Optional |
| | Citric Acid (pH adjustment to pH = 5.5 to 6.5) | Optional |
| | Water | Balance to 100% |

Liquid Viscosity of Formulation 1 = 5 cps@22° C.

TABLE 3

Antimicrobial Foam Soap Composition 2

| Component | Ingredient | Wt. % |
|---|---|---|
| Foamer | Cocamidopropyl Betaine | 3.00 |
| Foam booster, foam stabilizer | Suga ®Nate 100 (Sodium Decylglucosides Hydroxypropyl Sulfonate) | 3.00 |
| Foam stabilizer, sticky agent, cleanser | Colalipid ™ C (Cocamidopropyl PG-Dimonium Chloride Phosphate | 3.00 |
| Chelating Agent | Octaquest ® E30 (Trisodium Ethylenediamine Disuccinate) | 0.20 |
| Antibacterial Agent | Triclosan | 0.50 |
| Humectant | Propylene Glycol | 1.00 |
| Humectant/Moisturizer | Cola ™ Moist 200 (Hydroxypropyl Bis-Hydroxyethyldimonium Chloride) | 0.20 |
| Botanical Extracts - Moisturizing and Wound Healing | Allantoin ((2,5-Dioxo-4-Imidazolidinyl) urea) | 0.02 |
| Botanical Extracts - Moisturizing and Wound Healing | *Aloe Vera* | 0.02 |
| | Vitamin E | Optional |
| Freshness Handfeel | Frescolat ® MGA (Menthone Glycerin Acetal) | Optional |
| | Citric Acid (pH adjustment to pH = 5.5 to 6.5) | Optional |
| | Water | Balance to 100% |

Liquid Viscosity of Formulation 2 = 5 cps@22° C.

TABLE 4

Antimicrobial Foam Soap Composition 3

| Component | Ingredient | Wt. % |
|---|---|---|
| Foamer | Cocamidopropyl Betaine | 3.00 |
| Foam booster, foam stabilizer | Suga ®Nate 100 (Sodium Decylglucosides Hydroxypropyl Sulfonate) | 3.00 |
| Foam stabilizer, sticky agent, cleanser | Colalipid ™ C (Cocamidopropyl PG-Dimonium Chloride Phosphate | 3.00 |
| Foam booster | Suga ®Quat S1010 (Stearyldimoniumhydroxypropyl Decylglucosides Chloride) | 3.00 |
| Chelating Agent | Octaquest ® E30 (Trisodium Ethylenediamine Disuccinate) | 0.20 |
| Antibacterial Agent | Triclosan | 0.50 |
| Humectant | Propylene Glycol | 1.00 |
| Humectant/Moisturizer | Cola ™ Moist 200 (Hydroxypropyl Bis-Hydroxyethyldimonium Chloride) | 0.20 |
| Botanical Extracts - Moisturizing and Wound Healing | Allantoin ((2,5-Dioxo-4-Imidazolidinyl) urea) | 0.02 |
| Botanical Extracts - Moisturizing and Wound Healing | *Aloe Vera* | 0.02 |
| | Vitamin E | Optional |
| Freshness Handfeel | Frescolat ® MGA (Menthone Glycerin Acetal) | Optional |
| | Citric Acid (pH adjustment to pH = 5.5 to 6.5) | Optional |
| | Water | Balance to 100% |

Liquid Viscosity of Formulation 3 = 20 cps@22° C.

Colalipid™ is a trademark of Colonial Chemical Inc, Suga®Nate and Suga®Quat are registered trademarks of Colonial Chemical Inc. INUTEC® is a registered trademark of ORAFTI; Octaquest® is a registered trademark of Innospec Inc. and Tauranol® is also a registered trademark of Innospec Inc. Frescolat® is a registered trademark of Haarmann & Reimer G.m.b.H.

Following mixing, the liquid compositions of Tables 2-4 were foamed with air using a hand-operated foaming apparatus of the class described in United States Publication No. US 2001/0042761 of Ophardt et al. and U.S. Pat. No. 5,635,469 to Fowler et al., the disclosures of which are incorporated herein by reference. Alternatively, a foaming device with a deformable reservoir (squeeze-type) could be used, if so desired. See U.S. Pat. No. 6,536,685 to Bennett, the disclosure of which is incorporated herein by reference.

Likewise the compositions set forth above may be air foamed in a wall mounted or counter mounted soap dispenser equipped with a suitable foaming device of the general class described in the foregoing references, that is having an air pump and a foraminous foam refining screen or other foraminous component. An automated, touchless foam dispenser (wall or counter mounted) may likewise be used in connection with the compositions of the present invention if so desired. See United States Patent Publication No. US 2006/0011655 of Ophardt, U.S. patent application Ser. No. 10/928,099, the disclosure of which is incorporated by reference.

Foam Generation and Analysis

The soap was pumped five times from an air foam dispenser and into a waste beaker. On the sixth pump, a small amount of the foamed soap was sampled and placed on a concave slide with a cover slip. The slide is placed on the stage of the stereomicroscope utilizing transmitted light. The foam is brought into focus and an image is immediately taken (0 seconds) and saved to file. Using a timer, an image is also taken (of the same area) at 30 seconds and at one 1 minute. Three frames per time interval are collected for each sample.

Since the light source generates heat, and heat has an effect on foam cell size, the light source is not turned on until sampling is ready to be performed. In the case of a series of soaps being tested, the light source should be turned off between samples and allowed to cool down.

A magnification of 64× was used for these particular soaps. The magnification chosen should allow for good resolution of small cells, as well as adequate area to capture large cells, at the three time intervals. Once the magnification is determined, the stereoscope must be calibrated for that magnification. Taking an image of a scale micrometer at the magnification used is recommended.

The analySIS® program is used to measure the perimeter of each foam cell. The data obtained for each time interval is saved to an Excel file. When working with saved images, the magnification and calibration of the image must be read back in each time prior to measuring.

Figure 1B:
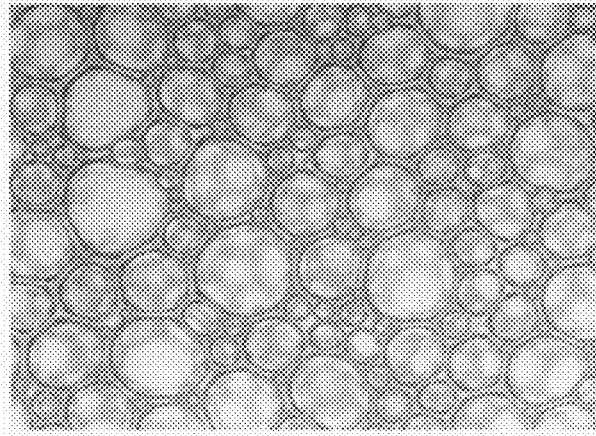
Figure 1C:
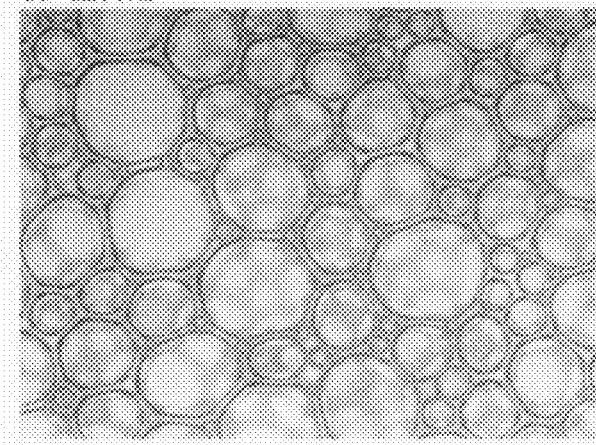
Figure 2A:
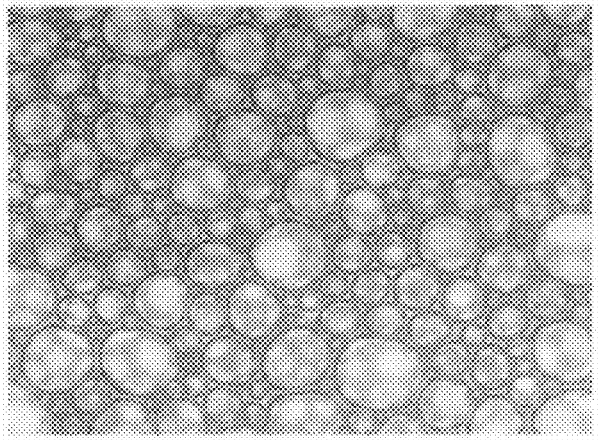
FIGS. 2A, 2B and 2C are photomicrographs of Foamed Composition No. 2 at 0, 30 and 60 seconds, respectively.
Figure 2B:
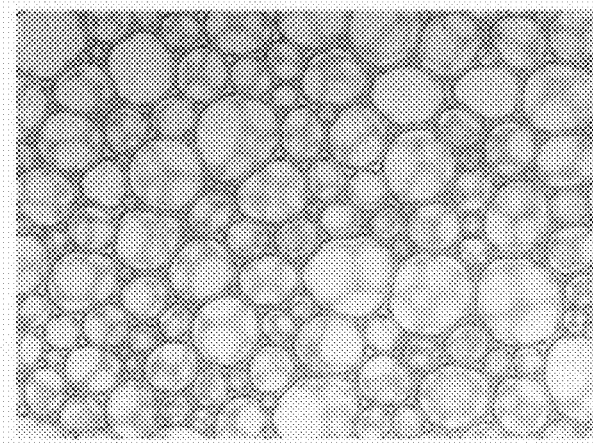
Figure 2C:
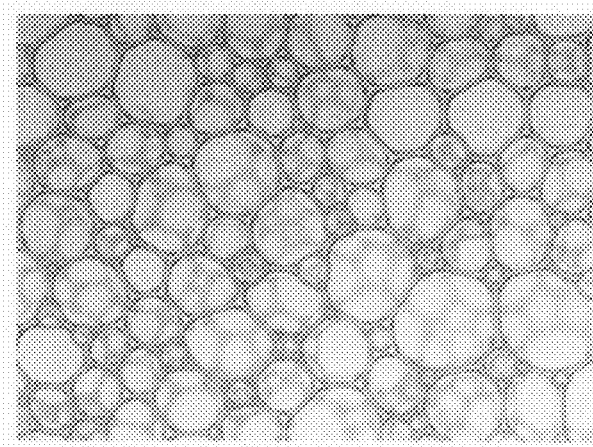
Figure 3A:
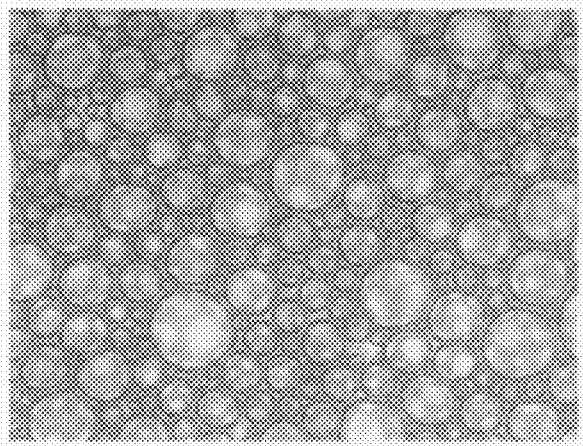
FIGS. 3A, 3B and 3C are photomicrographs of Foamed Composition No. 3 at 0, 30 and 60 seconds, respectively.
Figure 3B:
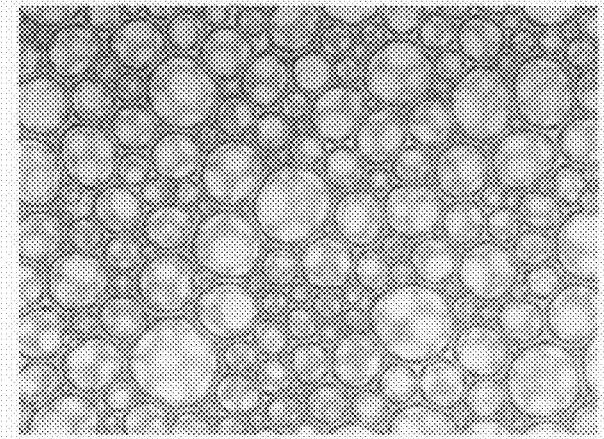
Figure 3C:
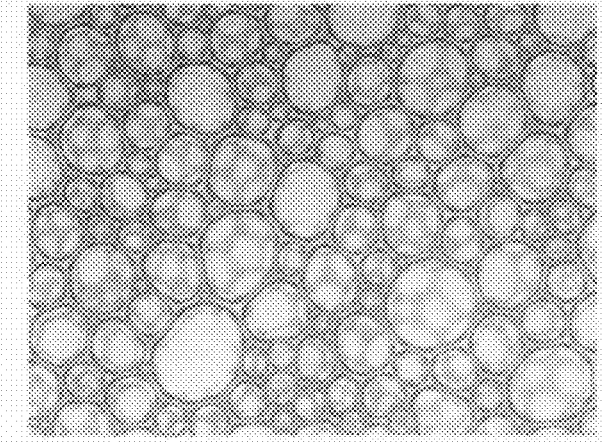

Results appear in Table 5 and in FIG. 1A through 3C.

TABLE 5

| | | Foam Stability | | |
|---|---|---|---|---|
| Hand Soap Formulation | | Composition 1 | Composition 2 | Composition 3 |
| Foam Cell | 0 Second | 121 | 127 | 111 |
| Diameter | 30 Second | 143 | 159 | 127 |
| (micron) | 60 Second | 169 | 181 | 153 |

In general, the average bubble size of the foamed composition ranges from about 50 microns to about 300 microns in diameter and the foam density ranges from about 0.01 g/cm$^3$ to about 0.25 g/cm$^3$ in most cases. A typical density range for the foam is from about 0.05 g/cm$^3$ to about 0.2 g/cm$^3$. It is seen in the photomicrographs that the foams of the invention exhibit a relatively uniform cell size, that is the cell size does not contain a large number of very small or very large bubbles but tends to have bubbles with diameters within a few multiples of the average cell size. The foam average diameter is calculated by dividing the average cell perimeter by Π.

It is seen from the photomicrographs that the foams exhibit remarkable stability at 60 seconds which is adequate time for the foams to be fully applied. Foam stability is calculated by dividing the average cell diameter at t=0 by the average cell diameter at t=60 seconds and accounts for the coalescence of cells over time.

There is thus provided in accordance with the present invention an aqueous antimicrobial foam hand soap which provides a glutinous tactile signal that includes: a) an antimicrobial agent; b) a foamable cleansing composition including one or more surfactants which readily foam with water and air; c) a glutinous composition including glutinous components selected from phospholipids, inulins, inulin-based surfactants and combinations thereof as well as water. In a first aspect of the invention the glutinous components are present in an amount of at least 5% by weight based on the weight of components other than water in the compositions. Generally the liquid compositions may be foamed with air to initial foam density (t=0) of from about 0.01 g/cm$^3$ to about 0.25 g/cm$^3$. The compositions may be foamed with air in a suitable non-propellant foamer to an average initial bubble size (i.e. t=0) of from about 50 to about 300 microns in diameter. More typically the average initial bubble size is from about 75 to about 150 microns in diameter. The compositions may suitably include more than 75%, more than 80%, more than 85% or more than 90% water. Remarkably, the compositions form stable foams even with very high water content.

The foamable cleansing compositions may include a betaine foaming agent such as cocamidopropyl betaine as well as other surfactants.

The glutinous components may include phospholipids and are generally present in an amount of from about 7.5% to about 40% by weight of ingredients other than water; typically, greater than 15% by weight of ingredients in the composition other than water. More than 20% by weight phospholipid (based on weight of ingredients other than water) is typical. There may be provided in some embodiments phospholipid in an amount of from about 15% to about 35% based on the weight of ingredients other than water such as from about 17.5% to about 30% based on the weight of ingredients other than water. Glutinous components may include inulin or an inulin-based surfactant such as inulin lauryl carbamate. When inulin is used as the primary glutinous component, inulin compounds are generally present in an amount of from about 5% by weight to about 15% by weight based on the weight of ingredients other than water, or in some cases from about 10% to about 20% based on the weight of ingredients other than water. Inulin compounds may be present in an amount of at least 10% by weight based on the weight of ingredients other than water.

The foamable compositions of the invention optionally include a chelating agent such as ethylene diamine disuccinate salt as well as an anti-bacterial agent such as triclosan. Other components such as humectants, emollients and so forth are typically included.

Most preferably, the composition is a sulfate free hand soap composition and consists essentially of one or more sulfonate surfactants, betaine surfactants, and carbamate surfactants. One preferred surfactant is cocoyl methyl isethionate surfactant. Another preferred group of surfactants are alkyl glucoside surfactants as noted above.

In another aspect of the invention there is provided an aqueous foam hand soap composition suitable for air foaming including: a) more than 75% water; b) a polysaccharide or polysaccharide surfactant selected from inulin, inulin surfactants, polyglucoside surfactants and mixtures thereof; and c) at least one additional foaming surfactant selected from betaine surfactants. These compositions include at least 5% of inulin, inulin surfactants, polyglucoside surfactants or mixtures thereof and the components are selected and present in amounts such that the composition exhibits a liquid viscosity at room temperature of from about 2.5 cps to about 35 cps as well as a 60 second foam stability of at least 0.5. Typically the composition exhibits a 60 second foam stability of from about 0.5 to about 0.9; and preferably at least about 0.6 or at least about 0.7. The composition may exhibit a viscosity at room temperature of from about 3 cps to about 7 cps in lower viscosity embodiments; or the compositions may exhibit a viscosity at room temperature of from about 15 cps to about 25 cps for higher viscosity compositions.

If so desired the aqueous foam hand soap compositions according to the invention may include at least 85% water and include cationic polysaccharide surfactants or sulfonated polysaccharide surfactants. One series of preferred embodiments includes at least about 20% by weight polysaccharide surfactant exclusive of water content. Optionally, the compositions may include at least 25% by weight polysaccharide surfactant, exclusive of water content or at least 30% by weight polysaccharide surfactant exclusive of water content. Polysaccharide surfactant containing compositions suitably include from about 20% by weight to about 50% by weight polysaccharide surfactant, exclusive of water content in many embodiments. Polysaccharide surfactant content from about 25% to about 45% based on the weight of ingredients other than water is typical. Further aspects should be apparent to one of skill in the art from the foregoing description and examples.

While the invention has been illustrated in connection with several examples, modifications to these examples within the spirit and scope of the invention will be readily apparent to those of skill in the art. In view of the foregoing discussion, relevant knowledge in the art and references discussed above in connection with the Background and Detailed Description, the disclosures of which are all incorporated herein by reference, further description is deemed unnecessary.

What is claimed is:

1. An aqueous foam hand soap composition suitable for air-foaming comprising:
   a) more than 75% water;
   b) a polysaccharide or polysaccharide surfactant selected from the group consisting of inulin, inulin surfactants, and mixtures thereof;
   c) a polyglucoside surfactant which is a sulfonate-functionalized polyglucoside surfactant; and
   d) at least one additional foaming surfactant selected from the group consisting of betaine surfactants, wherein the composition includes at least 5% by weight of components b) and c), and the components are selected and present in amounts such that the composition exhibits a liquid viscosity at room temperature of from about 2.5 cps to about 35 cps, as well as a 60-second foam stability of at least 0.5.

* * * * *